United States Patent [19]

Hess

[11] Patent Number: 4,669,488
[45] Date of Patent: Jun. 2, 1987

[54] RETENTION SKIRT FOR PACING ELECTRODE ASSEMBLY

[75] Inventor: Stanley R. Hess, Miami, Fla.

[73] Assignee: Cordis Corporation, Miami, Fla.

[21] Appl. No.: 785,234

[22] Filed: Oct. 7, 1985

Related U.S. Application Data

[62] Division of Ser. No. 479,854, Mar. 28, 1983, Pat. No. 4,564,023.

[51] Int. Cl.$^4$ ............................................. A61N 1/05
[52] U.S. Cl. ..................................... 128/785; 128/786; 128/419 P
[58] Field of Search .................... 128/419 P, 784–786, 128/642

[56] References Cited

U.S. PATENT DOCUMENTS

| | | |
|---|---|---|
| 724,913 | 4/1903 | Montgomery . |
| 3,719,190 | 3/1973 | Avery ............................ 128/418 |
| 3,835,864 | 9/1974 | Rasor et al. ................ 128/419 P |
| 3,902,501 | 9/1975 | Citron et al. .................... 128/418 |
| 3,939,843 | 2/1976 | Smyth ............................ 128/404 |
| 4,301,815 | 11/1981 | Doring ........................... 128/785 |
| 4,402,328 | 9/1983 | Doring .......................... 128/419 P |
| 4,407,271 | 10/1983 | Schiff ............................. 128/1 D |
| 4,409,994 | 10/1983 | Doring ........................... 128/785 |
| 4,419,819 | 12/1983 | Dickhudt ......................... 128/78 S |
| 4,506,679 | 3/1985 | Mann ............................. 128/78 S |

OTHER PUBLICATIONS

The Cordis Finned-Tip Pervenous Ventricular Lead Aug. 1979.

*Primary Examiner*—Kyle L. Howell
*Assistant Examiner*—Ruth S. Smith
*Attorney, Agent, or Firm*—Henry W. Collins; Thomas R. Vigil

[57] ABSTRACT

One embodiment of the electrode assembly is mounted at the distal end of a pacing lead including a lead body and at least one electrical wire conductor in the lead body and comprises a tip electrode including a tip and a connection of the tip to the wire conductor, and a partial skirt coupled to the lead body adjacent the tip. The partial skirt extends part way around the lead body backwardly from the tip. The partial skirt is capable of engaging trabeculae in a heart chamber for maintaining the electrode assembly in place and yet allows the electrode assembly to be removed when desired by the application of sufficient tension to the pacing lead to cause the partial skirt to fold back over itself as the pacing lead is withdrawn.

17 Claims, 9 Drawing Figures

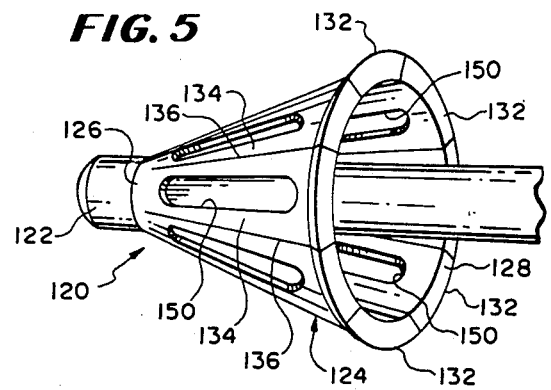
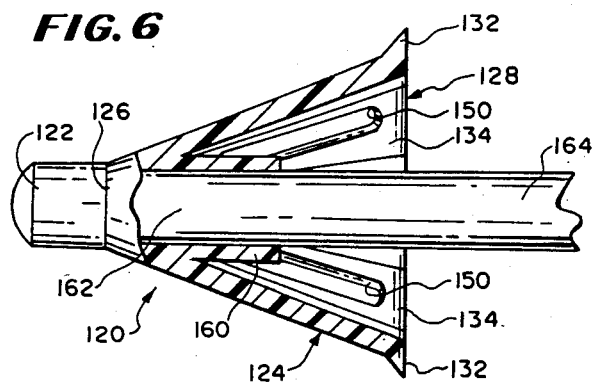
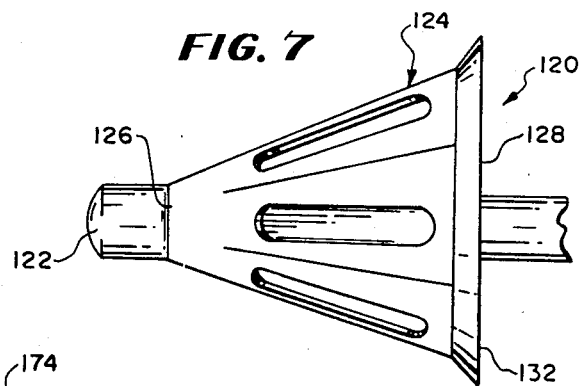
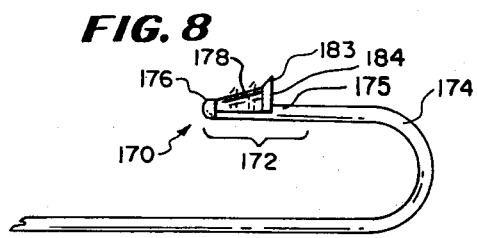
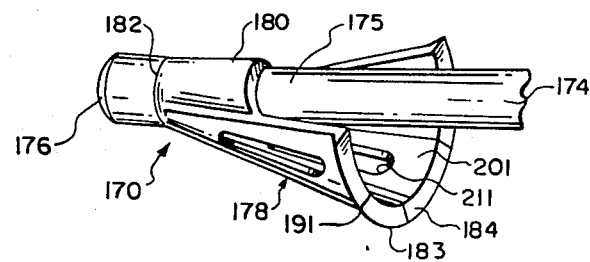

RETENTION SKIRT FOR PACING ELECTRODE ASSEMBLY

This is a division of application Ser. No. 479,854, filed Mar. 28, 1983 now U.S. Pat. No. 4,564,025.

BACKGROUND OF THE INVENTION

1. Field of the Invention

The present invention relates to a flexible retention skirt which forms part of an electrode assembly at the distal end of a pacing lead and which serves to hold an electrode tip of the assembly in a desired position within a heart.

2. Description of the Prior Art

Heretofore, various structures have been proposed for maintaining an electrode tip of an electrode assembly at the distal end of a pacing lead in a desired position within a heart. For example, in U.S. Pat. No. 3,902,501, there is disclosed an endocardial electrode having a plurality of pliant tines which are held against the electrode body during insertion and which are released and allowed to spread out when the electrode tip is in a desired position within a heart.

Also, in U.S. Pat. No. 3,719,190, there is disclosed a heart stimulation electrode with a conical positioning parachute which, when the electrode is inserted in a vein, permits blood flow in the vein to draw the electrode through the vein into the heart so that the electrode may be used with an external power source for stimulating the heart. When sufficient tension is applied to the pacing lead, the parachute will eventually invert to permit withdrawal of the electrode but will not return to its original shape in a heart cavity once it is inverted.

As will be described in greater detail hereinafter, the flexible retention skirt of the present invention provides for stable positioning of an electrode at the tip of an electrode assembly at the distal end of a pacing lead in a heart chamber, e.g. the atrium, by having a formation which engages heart tissue to minimize sliding back of the electrode, while at the same time having separable sections or being in the form of a partial skirt which facilitates removal of the electrode assembly when it is desired to do so by pulling on the pacing lead causing each skirt section or partial skirt to fold back over itself on retraction of the pacing lead and which sections or partial skirt will return to their or its' original orientation when the skirt is in an open space in a heart chamber for repositioning of the assembly in the heart chamber.

SUMMARY OF THE INVENTION

According to the invention there is provided an electrode assembly having an elongate axis and being mounted at the distal end of a pacing lead including a lead body and at least one electrical wire conductor in the lead body. The electrode assembly comprises a tip electrode including a tip and means for connecting the tip to the wire conductor and a partial skirt coupled to the lead body adjacent the tip which extends part way around the lead body between approximately 170° and approximately 210° about the elongate axis of said electrode assembly and which extends backwardly from the tip to a rear free edge of the skirt. The partial skirt is capable of engaging trabeculae in a heart chamber for maintaining said electrode assembly in place and the partial skirt by reason of having three free edges allows the electrode assembly to be removed when desired by the application of sufficient tension to the pacing lead such that the partial skirt easily folds back over itself as the pacing lead is withdrawn.

BRIEF DESCRIPTION OF THE DRAWINGS

FIG. 5 is a perspective view of still another embodiment of an electrode assembly comprising a tip electrode and a retention skirt constructed according to the teachings of the present invention.

FIG. 6 is a part sectional view of the retention skirt of the electrode assembly shown in FIG. 5.

FIG. 7 is a side view of the tip electrode and retention skirt shown in FIG. 5.

FIG. 8 is a perspective view of a further embodiment of an electrode assembly comprising a tip electrode and a retention skirt constructed according to the teachings of the present invention situated at the distal end of a J-atrial pacing lead.

FIG. 9 is an enlarged perspective view of the tip electrode and retention skirt shown in FIG. 8 viewing same from the inside of the J.

DESCRIPTION OF THE PREFERRED EMBODIMENT

Figure 1:
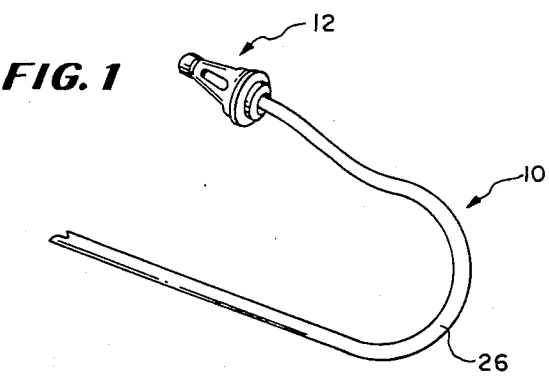
FIG. 1 is a perspective view of a pacing lead with an electrode assembly having a tip electrode and a retention skirt constructed according to the teachings of the present invention situated at the distal end of the pacing lead.

Referring now to the drawings in greater detail, there is illustrated in FIG. 1, a pacing lead 10 having an electrode assembly 12 which is mounted at the distal end thereof, and which is constructed according to the teachings of the present invention.

Figure 2:
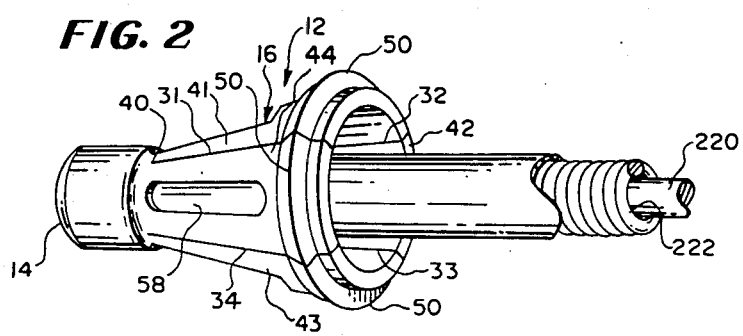
FIG. 2 is an enlarged perspective view of the tip electrode and the retention skirt shown in FIG. 1 with a portion of the pacing lead extending from the skirt broken away.
Figure 3:
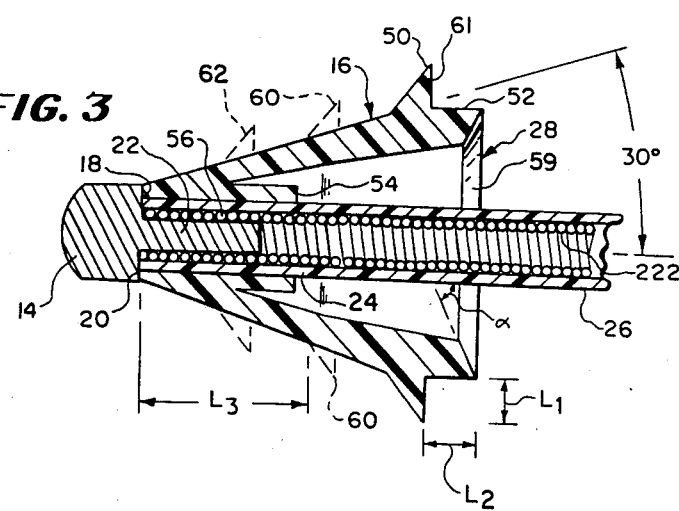
FIG. 3 is a sectional view of the tip electrode and the retention skirt shown in FIG. 2.

As shown in FIGS. 2 and 3, the electrode assembly 12 includes a tip electrode 14 and a retention cuff or skirt 16 which extends rearwardly from near the backside 18 of the tip electrode 14 and flares outwardly at an angle between 20° and 40° and preferably 30° to the elongate axis of the assembly 12, to form the skirt 16 with a generally conical shape.

The retention skirt 16 is constructed in accordance with the teachings of the present invention and has a forward edge 20 which abuts the backside 18 of the tip electrode 14. The skirt 16 extends conically rearwardly preferably a length of approximately 0.220±0.05 inch, from the tip electrode 14 about or within a terminal pin or shank 22 that extends rearwardly from and is integral with the tip electrode 14. The skirt 16 extends about a distal end portion 24 of a pacing lead body 26 and axially rearwardly to a rearward edge 28 of the skirt 16.

According to the teachings of the present invention, the retention skirt 16 has at least two, and in the illustrated embodiment, four slits 31-34 extending from the rearward edge 28 axially of the retention skirt 16 toward the forward edge 20 of the retention skirt 16 but not all the way to the forward edge 20. Each slit 31-34 will terminate a short distance before the forward edge 20 at an end 40 as shown in FIG. 2 and extends for 80 to 90% of the length of the skirt 16.

The slits 31–34 divide the retention skirt 16 into four sections 41–44, each of which has a radially outwardly extending annular quarter section spur 50. By annular quarter section is meant the spur 50 extends in, and on each skirt section 41–44 about the elongate axis of the assembly 12 through an arc of approximately 90°. As shown, each spur 50 is spaced inwardly from the rearward edge 28 of the skirt 16 and separated from the rearward edge 28 by a quarter section annular shoulder 52 in the skirt 16. Preferably, the spur 50 has a height $L_1$ of approximately 0.020 inch from shoulder 52 which has a width $L_2$ of approximately 0.020 inch.

Referring now to FIG. 3, it will be apparent that the retention skirt 16 also has a barrel or sleeve portion 54 which extends directly rearwardly from the forward edge 20 of the retention skirt 16, preferably a distance $L_3$ of approximately 0.165 inch and about the distal end portion 24 of the pacing lead 10. The barrel portion 54 serves to hold the distal end portion 24 of the pacing lead 10 about and in contact with the terminal pin or shank 22 extending rearwardly from the tip electrode 14 as shown.

The pacing lead 10 is of conventional construction and includes a coil of one or more wires or conductors, or as they are known in the art, filars 56, and the filars 56 at the distal end portion 24 of the pacing lead 10 have the insulation removed therefrom and are in mechanical and electrical contact with the shank 22. The inner diameter of the barrel portion 54 has the same diameter or a slightly smaller diameter than the outer diameter of the shank 22 so as to exert pressure on the shank 22 and/or lead body 26.

Also, if desired, each of the sections 41–44 of the retention skirt 16 can have an opening 58 therein to facilitate more the bending or folding over of the skirt sections 41–44 on themselves. Preferably, and as shown, each opening 58 is generally oblong in shape with each oblong opening 58 extending in a direction generally axially of the electrode assembly 12. Also, in one embodiment, each oblong opening 58 has a length of approximately ⅔ the length of the skirt 16. Such openings 58 are optional, however.

In one realization of the skirt 16, the skirt 16 was made of medical quality silicone rubber and had a length of approximately 0.220±0.05 inch and a thickness of approximately 0.015 to 0.020 inch. The barrel portion 54 had a length of approximately 0.165 inch. The spur 50 had a height $L_1$ of 0.015 inch and a width at its base of approximately 0.15 inch. The width $L_2$ of the shoulder 52 was approximately 0.020 inch. The back edge 28 was made normal to the axis of the electrode assembly 12 but preferably could have had a conical chamfer 59 at an angle $\alpha$ of approximately 60° to the axis of the assembly 12 as shown.

Also, one additional spur 60 with the same approximate dimensions of spur 50 was provided on each skirt section 41–44 as shown in phantom in FIG. 3. It may even be desirable to provide a third quarter annular spur 62 on each skirt section in addition to spurs 50 and 60.

In the embodiment of the electrode assembly 12 having the retention skirt 16 as shown in FIGS. 1–3, the electrode assembly 12 of the pacing lead 10 is inserted into the heart, such as through a vein, and when it is in proper position within a chamber of the heart, such as the atrium or ventricle, the physician makes tests to make certain that the tip electrode 14 is making proper contact with the endocardium for stimulating heart muscle tissue.

When the electrode assembly 12 is in proper position, the rearward edge 28 of the skirt 16, preferably with the chamfer 59, and back side 61 of each spur 50 adjacent shoulder 52 will engage trabeculae of the heart and serve to hold or maintain or retain the electrode assembly 12 in the now determined desired position. The back side 61 of each additional spur 60 will provide and serve the same function, namely, an anchoring function.

However, at a later time, it may be desirable to remove the electrode assembly 12 and pacing lead 10 and the slits 31–34 forming the skirt into four sections 41–44 facilitate and enable the pacing lead 10 to be easily removed from the heart merely by applying tension to the outer end of the pacing lead 10 and pulling it out of the heart. When this occurs, each section 41–44 of the skirt 16 will, when it is urged against the tissue, fold over on itself. The weakened area of each skirt section 41–44 between the front end of adjacent slits 31–34 created by the oblong opening 58 in each section 41–44 further facilitates this bending over. Then, further pulling of the pacing lead 10 will allow the pacing lead 10 to be pulled out of the heart chamber with the skirt sections 41–44 folded over on themselves.

Additionally, the opening 58 may also function as a holding means which provide for fibrotic growth therein to better hold the electrode assembly 12 with skirt 16 in place.

Also, it will be appreciated that for relocating the assembly 12 in a heart chamber once the assembly 12 has been dislodged from heart tissue, such as in the appendage of the atrium, by pulling on the lead body 26, the skirt sections 41–44 will resume their normal positions as shown in FIGS. 1–3 to permit relocating and reanchoring of the assembly 12.

Figure 4:
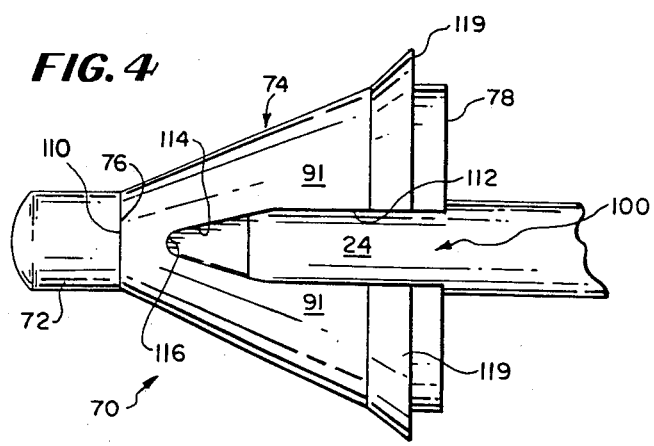
FIG. 4 is a side elevational view of another embodiment of an electrode assembly comprising a tip electrode and a retention skirt constructed according to the teachings of the present invention.

Referring now to FIG. 4, there is illustrated therein, another electrode assembly 70 constructed in accordance with the teachings of the present invention. This electrode assembly 70 has a tip electrode 72 similar or identical to the tip electrode 14 shown in FIGS. 1–3 and a skirt 74 which extends from a back side 76 of the tip electrode 72 conically rearwardly from the tip electrode 72 to a rearward edge 78 thereof. This retention skirt 74 is very similar to skirt 16 shown in FIG. 2 in that it has four sections 91, two of which are shown. Here, instead of having a slit, or at least two slits, the retention skirt 74 of FIG. 4 has at least two, and preferably four, axially extending notches 100 therein which extend from the rearward edge 78 of the skirt 74 inwardly toward, but not all the way to, the forward edge 110 of the retention skirt 74. Also, each notch 100 has a rear portion 112 which has one dimension and a forward portion 114 which tapers from the rear portion 112 to a rounded forward end 116 of the notch 100. If desired, the side of each notch 100 can be parallel without forward portion 114 and terminate in a radius. Also, the retention skirt 74 has four spurs 119.

In this embodiment, with the retention skirt 74 having notches 100, instead of slits 31–34, no oblong openings are provided such as the oblong openings 58 shown in FIGS. 2 and 3. However, if desired, oblong openings could be provided in the skirt sections 91. Alternatively, slits, like slits 31–34 of skirt 16 in FIG. 2, can be provided in the skirt 74 in addition to notches 100. The addition of slits may be preferred over openings 58.

The dimensions of the skirt 74 can be approximately the same as for skirt 16 and one or two additional spurs 119 can be provided on each skirt section 91 to assist in the anchoring of the assembly 70.

Referring now to FIGS. 5-7, there is illustrated therein, another embodiment of the electrode assembly of the present invention which is generally identified by the reference numeral 120. Here, the electrode assembly 120 has a tip electrode 122 similar to or the same as the tip electrodes 14 and 72 shown in FIGS. 3 and 4. However, in this embodiment, a retention skirt 124 modified somewhat from the retention skirt 16 shown in FIG. 3 is provided. Here, the retention skirt 124 has a forward edge 126 and a rearward edge 128. However, this conically shaped retention skirt 124 differs by having one spur formation 132 extending outwardly from the rear edge 128 of each skirt section 134 as shown. If desired, each skirt section 134 can have one or two additional spurs with the spurs extending around the skirt 124 at the same axial location of the spurs, e.g. spur formations 132, forming an annular collar about the skirt 124.

This retention skirt 124 is generally conical and is provided with eight slits 136 therein to divide the skirt 124 into the eight sections 134. Also, each section 134 can be provided with an oblong opening 150 extending axially of the electrode assembly 120 and skirt 124 thereof, if desired.

As shown in FIG. 6, the skirt 124 is also provided with a barrel or sleeve portion 160 which extends directly rearwardly from the tip electrode 122 and is configured and dimensioned so as to receive therein, distal end portion 162 of a pacing lead 164.

In this electrode assembly 120 where eight skirt sections 134 are provided, such sections 134 have a shorter width that may further facilitate withdrawal of the electrode assembly 120 from a heart chamber. In this respect, if obstructing tissue is encountered, only one or two of the skirt sections 134 may be forced to fold over while the others will remain in the position shown while the electrode assembly 120 is being retracted from an anchored position.

Also, although only one spur formation 132 is shown on each skirt section 134, as noted above, one or two additional spurs can be provided on each skirt section 134 to assist in the anchoring thereof in trabeculae.

To further minimize trauma to tissue and yet at the same time provide a retention function, it may be desirable to provide an electrode assembly with a retention skirt that does not extend completely around the electrode assembly and distal end portion of a pacing lead. Such a construction of an electrode assembly is shown in FIGS. 8 and 9 and is generally identified by reference numeral 170. Here, a distal end portion 172 of a J-atrial pacing lead 174 is shown provided with a J-shaped set as shown in FIG. 8. Then, at the distal end 175 of the lead 174, there is mounted the electrode assembly 170 comprising at least a tip electrode 176 and a retention skirt 178 which has a semi-conical configuration as shown. Here again, the retention skirt 178 includes a barrel portion 180 which extends from a forward end 182 of the skirt 178 rearwardly in line with the tip electrode 176 a short distance for receiving the distal end 175 of the J-atrial pacing lead 174 for holding same within the electrode assembly 170 and about a terminal pin or shank (not shown) extending rearwardly from the tip electrode 176. The semi-conical retention skirt 178 then extends conically or in a flared manner rearwardly from a forward edge 182 of the skirt 178 to a semi-circular rearward edge 184 thereof and on the outside of the J-shaped distal end portion 172 as shown in FIG. 8. A spur formation 183 extends radially outwardly from the rearward edge 184 as shown.

It will be noted that this retention skirt 178 is very similar to the retention skirt 74 shown in FIGS. 5-7 having substantially the same dimensions and being made of substantially the same material except that half of the skirt is removed. In this embodiment of the electrode assembly 170 and skirt 178, three slits 191 are provided so as to divide the skirt into four sections 201. Also, each one of the sections 201 is provided with an oblong opening 211 extending axially of the skirt and electrode assembly.

Although shown with three slits 191, it may be desirable to provide only one slit 191 so as to divide the skirt into only two sections 201. Still further, it may be that no slits are needed in this embodiment since only a partial or half skirt 178 is provided, which, because of one or more oblong openings 211 therein, can easily fold over on itself when the pacing lead 174 is withdrawn from the body and will easily return to its original position. Thin, axially extending portions of skirt are provided between openings. Also, in a partial skirt with one oblong opening, thin, axially extending portions of skirt are provided between each axial edge of the opening and an axial edge of the skirt.

The partial skirt 178 or sections 201 thereof are preferably provided with one or more additional partially annular spurs similar to spur formation 183. Further, the partial skirt 178 will extend around the axis of the electrode assembly 170 through an arc of approximately 170° to 200° on the outside of the J. It could, if desired, extend on the other side or inside of the J. Also, skirt 178 can be provided with or without oblong openings 211 and with or without slits 191. Preferably, skirt 178 is provided with two slits 191, three sections 201 and three oblong openings 211. Otherwise, the skirt 178 has dimensions similar to the dimensions of skirt 16 shown in FIGS. 1-3 and is made of medical quality silicone rubber.

In use, the distal end portion 172 of the lead 174 is straightened with a stylet and inserted in the atrium of a heart. Then the stylet is withdrawn and the distal end portion 172 resumes its J shape set as shown in FIG. 8. The pulling back on the lead 174 will pull the tip or distal end 175 into the appendage of the atrium. The skirt 178 on the outside of the J forces the electrode to one side of the appendage and into good electrical contact with heart tissue.

In positioning any of the electrode assemblies 12, 70, 120 and 170 shown respectively in the various FIGS. 1-9, it is usually necessary to use a stylet 220 (FIG. 2) which is inserted through cylindrical envelope or lumen 222 (FIG. 2) which exits within coiled filars 56 within the pacing lead body 26.

After the pacing lead is first inserted into a body with a stylet 220, the stylet 220 is then manipulated by a physician to place the electrode assembly 12, 70, 120, or 170, and more particularly, the tip electrode 14, 72, 122, 176 thereof, into a proper desired position so that it can contact the myocardium in a heart chamber, such as the atrium.

A portion of the stylet 220 received within the pacing lead 10, 164, 174 is shown in FIG. 2. Once a tip electrode is properly located in a heart chamber, the stylet 220 is removed from the various assemblies and the retention skirt e.g. skirts 16, 74, 124, 178 of the present invention as shown in the respective FIGS. 1-9 serve to hold the electrode assembly, e.g., assemblies 12, 70, 120, 170 anchored in place with the tip electrode 14, 72, 122, 176 in good electrical contact with heart tissue.

From the foregoing description, it will be apparent that the electrode assembly 12, 70, 120 or 170 of the present invention, and particularly the novel retention skirt 16, 74 124 or 178 thereof, provide a number of advantages, some of which have been described above and others of which are inherent in the invention. Most importantly, the skirt 16, 74 124 or 178 provides means for facilitating and assisting anchoring and retention of the electrode assembly 12, 70, 120, 170 in place within a chamber of the heart, particularly the atrium, while at the same time permitting each retention skirt to be distorted and folded over on itself when it is desired to remove the electrode assembly 12, 70, 120, 170 from the heart chamber by pulling the pacing lead 10, 164, 174, followed by return of the skirt 16, 74, 124 or 174 to its original shape when disposed in an open space within a heat chamber thereby permitting repositioning and reanchoring thereof.

Moreover, it will be apparent that modifications can be made to the electrode assembly 12, 70, 120 or 170 and novel flexure retention skirt 16, 74, 124 or 178 thereof, without departing from the teachings of the present invention. Accordingly, the scope of the invention is only to be limited as necessitated by the accompanying claims.

I claim:

1. An electrode assembly having an elongate axis and being mounted at the distal end of a pacing lead including a lead body and at least one electrical wire conductor in the lead body, said electrode assembly comprising a tip electrode including a tip and means for connecting the tip to the wire conductor and a partial skirt coupled to the lead body adjacent said tip, extending part way around said lead body between approximately 170° and approximately 210° about the elongate axis of said electrode assembly and extending backwardly from said tip to a rear free edge of said skirt, said partial skirt being capable of engaging trabeculae in a heart chamber for maintaining said electrode assembly in place and said partial skirt by reason of having three free edges allowing said electrode assembly to be removed when desired by the application of sufficient tension to the pacing lead such that said partial skirt easily folds back over itself as the pacing lead is withdrawn.

2. The electrode assembly of claim 1 wherein said partial skirt extends approximately half way around said pacing lead.

3. The electrode assembly of claim 1 wherein said skirt defines an approximately half conical envelope about the distal end of said pacing lead having said electrode tip.

4. The electrode assembly of claim 1 having means for separating said partial skirt into at least two separate sections.

5. The electrode assembly of claim 4 wherein said skirt has a front edge and said rear edge and said means for separating said partial skirt into separate sections are defined by at least one slit extending axially part way through said skirt from said rear edge thereof toward but not all the way to said front edge thereof.

6. The electrode assembly of claim 4 wherein at least one of said sections has a hole therein which facilitates folding over of the said section onto itself on removal of said assembly by reason of the reduced material in the said section.

7. The electrode assembly of claim 6 wherein said hole is oblong in the axial direction of said skirt.

8. The electrode assembly of claim 1 in combination with a J-atrial pacing lead having a J-shaped distal end portion with said electrode assembly being situated at the distal end of said pacing lead and wherein said partial skirt has a semi-conical shape partially surrounding said pacing lead and is situated on the outside of short portion of the J and extends away from a long portion of the J in said distal end portion of said pacing lead.

9. The electrode assembly of claim 8 wherein said partial skirt has at least one oblong axially extending opening therein which provides thin skirt portions on either side thereof between an axial side of the opening and an axial edge of said partial skirt and extending axially in said partial skirt, said thin skirt portions facilitating folding over of said partial skirt by reason of reduced material in said skirt.

10. The electrode assembly of claim 1 wherein said partial skirt has at least one spur extending radially outwardly from said partial skirt.

11. The electrode assembly of claim 10 wherein said spur extends arcuately around said partial skirt.

12. The electrode assembly of claim 10 wherein said spur extends from said partial skirt at or adjacent said rear edge of said partial skirt.

13. The electrode assembly of claim 12 wherein said partial skirt has at least two spurs extending outwardly therefrom, said second spur being spaced forwardly of said first named spur.

14. The electrode assembly of claim 12 wherein said partial skirt has three spurs extending outwardly therefrom, each spaced from each other with the second and third spurs spaced forwardly on said partial skirt from said first named spur.

15. The electrode assembly of claim 10, wherein said spur extends in an arc about said partial skirt and outwardly a distance of approximately 0.020 inch from said partial skirt.

16. The electrode assembly of claim 1 wherein said partial skirt is made of medical quality silicone rubber and has a thickness of approximately 0.020 inch.

17. The electrode assembly of claim 1 having means for separating said partial skirt into at least two thin skirt portions, said means being defined by one oblong axially extending opening in said skirt which provides said thin skirt portions on either side thereof between an axial side of the opening and an axial edge of said partial skirt, said thin skirt portions extending axially in said partial skirt and facilitating folding over of said partial skirt by reason of reduced material in said skirt.

* * * * *